United States Patent [19]
Sjögren et al.

[11] Patent Number: 5,236,956
[45] Date of Patent: Aug. 17, 1993

[54] COMPOUNDS FOR THE TREATMENT OF URINARY INCONTINENCE

[75] Inventors: Christer Sjögren, Viken; René Mollberg, Helsingborg; Sten Kelfve, Ödåkra, all of Sweden

[73] Assignee: Kabi Pharmacia Aktiebolag, Uppsala, Sweden

[21] Appl. No.: 771,813

[22] Filed: Oct. 7, 1991

Related U.S. Application Data

[63] Continuation of Ser. No. 430,880, Nov. 2, 1989, abandoned.

[30] Foreign Application Priority Data

Nov. 4, 1988 [SE] Sweden ................ 8804003

[51] Int. Cl.$^5$ ................ C07C 237/20; A61K 31/165
[52] U.S. Cl. ................ 514/617; 514/331; 514/622; 546/234; 564/161; 564/171; 564/181
[58] Field of Search ................ 564/181, 161, 171; 514/617, 622

[56] References Cited

U.S. PATENT DOCUMENTS

| 2,009,144 | 9/1934 | Miescher et al. | 564/181 |
|---|---|---|---|
| 2,658,076 | 11/1953 | Krimmel | 564/161 |
| 2,733,256 | 1/1956 | Krapcho et al. | 564/171 |
| 2,746,992 | 5/1956 | Goldberg | 564/181 |
| 2,831,892 | 4/1958 | Dornfeld | 564/181 |
| 2,862,965 | 12/1958 | Lott et al. | 564/171 |
| 2,932,645 | 4/1960 | Sumerford et al. | 564/171 |
| 3,808,213 | 4/1974 | Clemence et al. | 544/391 |

FOREIGN PATENT DOCUMENTS

| 0364123 | 4/1990 | European Pat. Off. |
|---|---|---|
| 2319337 | 2/1977 | France . |
| 2333501 | 7/1977 | France . |
| 2340724 | 9/1977 | France . |
| 2421891 | 11/1979 | France . |
| 2421892 | 11/1979 | France . |
| 1560839 | 2/1980 | United Kingdom . |
| 1574046 | 9/1980 | United Kingdom . |

OTHER PUBLICATIONS

Olin Mathieson Corporation, *Chem. Abst.*, vol. 64, 19504 (1966).

W. Chiti, *Farmaco* 15:29-43, "Ureides Of Local Anesthetic Action." (1960).

D. K. De Jongh, et al., *Arch. Int. Pharmacodyn.*, 103:100-119, "Substituted Phenylpropylamines: II. Pharmacological Properties of Basic Butyronitirles and Butyramides." (1955).

(List continued on next page.)

*Primary Examiner*—Richard L. Raymond
*Assistant Examiner*—Scott C. Rand
*Attorney, Agent, or Firm*—Pravel, Hewitt, Kimball & Krieger

[57] ABSTRACT

The invention concerns compounds having the formula I

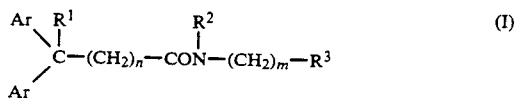

wherein
Ar is a phenyl or benzyl group which is optionally substituted with hydroxy or alkoxy;
$R^1$ is hydrogen, lower alkyl, lower alkoxy, hydroxy;
$R^2$ is hydrogen, lower alkyl;
$R^3$ is $NR^4R^5$, wherein
$R^4$ and $R^5$ which can be the same or different, are lower alkyl, or wherein $R^4$ and $R^5$, when taken together, form a ring with the nitrogen atom, whereby said ring optionally is substituted with lower alkyl;
n is 0 or 1;
m is 2 or 3 and
their salts with physiologically acceptable acids and when the compounds can be in form of optical isomers, the racemic mixture and the individual isomers, for the treatment of disorders of the urinary bladder.

6 Claims, No Drawings

OTHER PUBLICATIONS

C. Sjögren and K.-E. Andersson, *Acta Pharmacol., Et Toxicol.*, 44:228-234, "Effects of Cholinoceptor Blocking Drugs, Adrenoceptor Stimulants, and Calcium Antagonists on the Transmurrally Stimulated Guinea-pig Urinary Bladder In Vitro and In Vivo." (1979).

M. M. Winbury and D. H. Papierski, *Arch. Int. Pharmacodyn.*, 108:215-224, "Suppression of Experimental Ventricular Arrhythmias in the Unanesthetized Dog with N-($\gamma$-isopropylaminopropyl)-$\alpha$, $\alpha$-diphenylacetamide hydrochloride." (1956).

L. Zappia, et al., *J. Urology*, 136:739-742, "Action of Pirenzepine on the Human Urinary Bladder In Vitro." (1986).

Kuznetsov et al., *Chem. Abs.*, vol. 59: 12604h-12605b (1963).

Stecher, Ed., et al., *The Merck Index*, Eighth Edition, p. 358 (1968).

Shklyaev et al., *Chem. Abs.* 85:159217c (1976).

Levine et al., *Chemical Abstracts*, vol. 52, 3133i (1958).

COMPOUNDS FOR THE TREATMENT OF URINARY INCONTINENCE

This is a continuation of co-pending application Ser. No. 430,880 filed on Nov. 2, 1989, now abandoned.

The present invention concerns compounds being of potential use for the treatment of urinary incontinence. Specifically the invention concerns compounds which may be used for the treatment of disorders of the urinary bladder related to changes in the function of the urinary bladder smooth muscle or its sensory and motor innervation.

Two compounds, Terodiline, (N-t-butyl-3,3-diphenyl-1-methylpropylamine) and Oxybutynine, (2-cyclohexyl-2-hydroxy-2-phenylacetic acid 4-(diethylamino)-2-butynyl ester) are clinically used today for the treatment of urinary incontinence, specifically urge incontinence. Both these compounds are anticholinergic and in addition to their ability to relax the urinary bladder smooth muscle and retain urine they have the other classical anticholinergic properties resulting in e.g. an increase of the heart rate by blocking the vagus nerve (tachycardia), inhibition of the salivary and broncial secretion, inhibition of the accommodation of the eye etc. As the main actions of all members of anticholinergic or antimuscarinic drugs are qualitatively similar to those of the best known member, atropine, the terms atropinic and atropine-like are also appropriately used.

The U.S. Pat. No. 2,009,144 discloses a group of compounds which are said to have valuable therapeutic properties and "approximate atropine in value". The form "approximate atropine in value" is not further explained and it is therefore reasonable to believe that this group of compounds should be used for the treatment of the same disorders as atropine, i.e. for the treatment of spastic contractile states of the gastrointestinal channel, of ulcus duodeni, hypersecretion, hyperhidrosis, bradycardia and Parkinsonism. However, to the best of our knowledge no one has suggested the compounds according to this patent would be of any use for the treatment of urinary bladder disorders. This is true also for the compounds disclosed in the French patent applications 2333501, 2340724 and 2421891.

The French patent application 2 333 501 discloses a group of compounds, which are stated to have anticonvulsive and antiaggressive properties. In the French patent application 2 340 724 a group of compounds having anti-arrythmic properties are disclosed, whereas the French patent application 2 421 891 discloses a group of compounds which are stated to be useful for respiratory disorders.

The present invention concerns compounds, some of which are new, for the treatment of disorders of the urinary bladder. Specifically the invention concerns compounds which essentially selectively influences the urinary bladder and have a minimum of other anticholinergic side effects. It has been found that the compounds according to the invention has essentially no effects on the heart function, the salivation or accommodation of the eye. The compounds according to the present invention can be characterized by the following general formula I

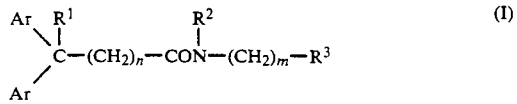

wherein
Ar is a phenyl or benzyl group which is optionally substituted with hydroxy or alkoxy;
$R^1$ is hydrogen, lower alkyl, lower alkoxy, hydroxy;
$R^2$ is hydrogen, lower alkyl;
$R^3$ is $NR^4R^5$, wherein
$R^4$ and $R^5$ which can be the same or different, are lower alkyl, or wherein $R^4$ and $R^5$, when taken together, form a ring with the nitrogen atom, whereby said ring optionally is substituted with lower alkyl;
n is 0 or 1;
m is 2 or 3 and
their salts with physiologically acceptable acids and when the compounds can be in form of optical isomers, the racemic mixture and the individual isomers.

It is understood that as used herein the term "lower" in "lower alkyl" or "lower alkoxy" means alkyl having 1-4 atoms inclusive. It is preferred that $R^1$ is hydrogen, hydroxy or methyl and that $R^2$ is hydrogen or methyl. As regards $R^4$ and $R^5$ it is preferred that at least one of these substituents is a branched alkyl, such as isopropyl, isobutyl, sek-butyl or tert-butyl. It is preferred that Ar is nonsubstituted phenyl, n is 0 and $R^4$ and $R^5$ when forming a ring together with the nitrogen atom, form a piperidine ring, which optionally is substituted with methyl groups.

The compounds of formula I can form salts with physiologically acceptable acids, organic and inorganic, and the invention comprises the free bases as well as the salts thereof. Examples of acid addition salts include the hydrochloride, hydrobromide, hydrogen fumarate, methanesulfonate and the like.

The following compounds are specifically preferred:
N-methyl-N-[3-(N-tert-butyl-N-methylamino)-propyl]-2,2-diphenyl-acetamide.
N-methyl-N-(3-diisopropylaminopropyl)-2,2-diphenylacetamide.
N-methyl-N-(2-diisopropylaminoethyl)-2,2-diphenylacetamide.
N-methyl-N-(3-diethylaminopropyl)-2,2-diphenylacetamide.
N-methyl-N-(3-diisopropylaminopropyl)-2,2-diphenyl-2-hydroxyacetamide
N-methyl-3-(2,6-dimethyl-piperidinopropyl)-2,2-diphenylacetamide.
N-methyl-N-(3-dimethylaminopropyl)-2,2-diphenylacetamide.
N-methyl-2-(2,2,6,6,-tetramethylpiperidinoethyl)-2,2-diphenylacetamide
N-methyl-N-(3-di-sek-butylaminopropyl)-2,2-diphenylacetamide.
N-(2-diisopropylaminoethyl)-2,2-diphenylacetamide.
N-methyl-N-(2-diisopropylaminoethyl)-2-methyl-2,2-diphenylacetamide.

Within the scope of the present invention are also new compounds having the same properties as the compounds of the general formula I and which can be defined by the following general formula II

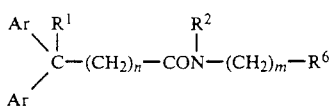

$$\text{Ar}_2\text{C}(R^1)(CH_2)_n-CON-(CH_2)_m-R^6 \quad (II)$$

wherein

Ar is a phenyl or benzyl group which is optionally substituted with hydroxy or alkoxy;

$R^1$ is hydrogen, lower alkyl, lower alkoxy, hydroxy;

$R^2$ is hydrogen, lower alkyl;

$R^6$ is $NR^7R^8$ wherein $R^7$ and $R^8$ which can be the same or different, are lower alkyl, whereby at least one alkyl group is branched and the total number of carbon atoms in $R^7$ and $R^8$ is at least 4;

n is 0 or 1;

m is 2 or 3 and as well as their salts with physiologically acceptable acids and, when the compounds can be in the form of optical isomers, the racemic mixture and the individual enantiomers.

The compounds according to the invention can be prepared according to conventional methods. These methods include the reaction of carboxylic acids or reactive derivatives thereof such as halides, anhydrides or lactones with amino compounds such as amino alcohols, amino alkyl halides, secondary amines, primary amines or amino nitriles. The starting materials are mostly commercially available or can be prepared by methods known from the literature.

Specifically the compounds according to the invention can be prepared according to the following methods:

a) a compound of the general formula III, $$\text{Ar}_2C(R^1)(CH_2)_nCO\text{-p} \quad (III)$$

wherein Ar, $R^1$ and n are as previously defined and p is OH, is reacted with with an amine having the general formula $$HN(R^2)(CH_2)_mR^3$$

wherein $R^2$, m and $R^3$ are as previously defined; to form a compound of the general formula I b) a compound of the general formula IV, $$\text{Ar}_2C(R^1)(CH_2)_nCO\text{-q} \quad (IV)$$

wherein Ar, $R^1$ and n are as previously defined and q is a carbonyl activating group such as chloro, bromo, anhydride, unsymmetrical anhydride, derivatives formed with cartodiimides, carbonyldiimidazoles, acetoxyacetylene, lactones and alkyl-, arylesters; is reacted with with an amine having the general formula $$HN(R^2)(CH_2)_mR^3$$

wherein $R^2$, m and $R^3$ are as previously defined, to form a compound of the general formula I c) a compound of the general formula V $$\text{Ar}_2C(R^1)(CH_2)_nCON(R_2)(CH_2)_m\text{-r} \quad (V)$$

wherein Ar, $R^1$, n, $R_2$ and m are as previously defined and r is p-toluenesulfonyloxy, benzenesulfonyloxy, methanesulfonyloxy, chloro and bromo; is reacted with an amine having the general formula $$HNR^4R^5$$

wherein $R^4$ and $R^5$ are as previously defined; to form a compound of the general formula I and d) a compound of the general formula VI $$\text{Ar}_2C(R^1)(CH_2)_nCON(R_2)H \quad (VI)$$

wherein Ar, $R^1$, n and $R_2$ are as previously defined; is reacted with s—$(CH_2)_mNR^4R^5$ wherein m, $R^4$ and $R^5$ are as previously defined and s is p-toluensulfonyloxy, benzenesulfonyloxy, methanesulfonyloxy, chloro and bromo, to form a compound of the general formula I The present invention also concerns a method for the treatment of disorders of the urinary bladder related to alterations in the function of the urinary bladder smooth muscle or its sensory or motor inervation in human or non-human mammals, which method comprises administering an effective, non-toxic amount of a compound having the general formula I or a pharmaceutically acceptable salt thereof, to human or non-human mammals in need of such treatment.

The compounds according to this invention may be administered by way of oral, sub-lingual, transdemmal, rectal, parenteral, intravesical, inhalation, insufflation or intranasal routes, being usually employed in the form of a pharmaceutical composition. Such compositions are prepared in a manner well-known in the pharmaceutical art and comprise the active compound associated with a pharmaceutically acceptable carrier.

The compositions are preferably formulated in a unit dosage form, each dosage containing from about 0.05 to about 500 mg, more usually about 5 to about 300 mg of the active ingredient. The term "unit dosage form" refers to physically discrete units suitable as unitary dosages for human subjects and other mammals, each unit containing a predetermined quantity of the active compound calculated to produce the desired therapeutic effect, in association with the required pharmaceutical carrier.

The compounds according to the invention are effective over a wide dosage range. For example, dosages per day will normally fall within the range of about 0.001 to about 50 mg/kg of body weight. In the treatment of adult humans, the range of about 0.002 to about 10 mg/kg in single or divided doses, is preferred. The compounds according to the invention are also expected to be effective by instillation in the urinary bladder in doses of 0.0005 to 1 mg/kg. However, it will be understood that the amount of the active compound actually administered will be determined by a physician, in the light of the relevant circumstances including the condition to be treated, the chosen route of administration, the age, weight, and response of the individual patient, and the severity of the patient's symptoms, and therefore the above dosage ranges are not intended to limit the scope of the invention in any way. As used herein the terms "pharmaceutical compositions" and "pharmaceutically acceptable" include compositions and ingredients for both human and veterinary use.

The present invention also comprises a pharmaceutical composition for the use in the treatment of urinary disorders of the type mentioned above, which comprises an effective amount of the active compound having the general formula II or a pharmaceutically acceptable salt or hydrate thereof and a pharmaceutically acceptable carrier. Such compositions may be prepared in the manner as described hereinbefore.

The following examples are intended to illustrate but not to limit the scope of the invention, although the compounds named are of particular interest for our intended purposes.

The structures of the compounds found in Examples 1–12 are confirmed by NMR and elementary analysis. The NMR data are recorded using a Bruker AC 250. Melting points are determined with a Mettler FP-apparatus.

EXAMPLE 1

N-(2-diisopropylaminoethyl-)-2,3-diphenyl-propionamide hydrochloride

To a solution of 154.2 g (1,1 mole) of hexamethylenetetramine in 600 ml of chloroform at reflux, was added dropwise a solution of 200.2 g (1,0 mole) of N,N-diisopropylaminoethyl chloride hydrochloride, previously converted to the baseform. After about 10 minutes crystals were formed. The mixture was refluxed for 2 h, cooled in an icebath, filtered and the crystals were collected and dried. The crystalline hexamethylenetetramine complex was added to 600 ml ethanol. Concentrated hydrochloric acid was added to pH 2. The solution was heated at about 60° C. for 1 hour. The remaining solution was evaporated to dryness and extracted with ethanol. The ethanol was evaporated to dryness and the product was converted to the baseform with dilute sodium hydroxide and extracted with ether. The ether was evaporated and the remaining oil was distilled. Boiling point 96° C./8 mm Hg.

Yield 106.4 g (74%) of 2-N,N-diisopropylaminoethylamine.

4.9 g (20 mmole) of 2,3-diphenylpropionyl chloride were dissolved in 25 ml of methylene chloride and added dropwise to a solution of 8.7 g (40 mmole) of the above described N,N-diisopropylaminoethylamine. The mixture was stirred at 20° C. for 12 hours and washed with dilute hydrochloric acid to remove excess of amine. The methylene chloride layer was evaporated and the residue was crystallised from dioxane/ether.

Yield 6.2 g (80%) of N-(2-diisopropylaminoethyl-)-2,3-diphenyl-propionamide hydrochloride. Melting point 130° C.

EXAMPLE 2

N-(2-diisopropylaminoethyl)-2-methoxy-2,2-diphenylacetamide hydrochloride 5.7 g (25 mmole) of bensilic acid were refluxed with 150 ml thionyl chloride until the evolution of hydrogen chloride ceased (about 2 hours). The solution was evaporated to dryness at 60° C. The residue was treated with hexane and a small amount of unreacted product was filtered. The hexane solution was evaporated and the remaining oil was distilled under reduced pressure. Boiling point 157°–60° C./8 mm Hg.

Yield 4.2 g (63%) of 2-chloro-2,2-diphenylacetyl chloride.

4.0 g (15 mmole) of the above described acid chloride in 20 ml dioxane were slowly added to a solution of 2.2 g (15 mmole) of N,N-diisopropylaminoethylamine in 20 ml dioxane. The solution was stirred for 2 hours at 20° C. Then the dioxane was removed by distillation and the residue was boiled with 50 ml of methanol for 8 hours to convert the 2-chloro into a methoxy group. The solution was evaporated and the residue was dissolved in 50 ml of methylene chloride. This solution was shaken with dilute hydrochloric acid and the organic phase was evaporated to dryness. The product was recrystallised from dioxane/ether.

Yield 4.4 g (73%) of N-(2-diisopropylaminoethyl)-2-methoxy-2,2-diphenylacetamide hydrochloride. Melting point 189° C.

EXAMPLE 3

N-methyl-N-(2-diisopropylaminoethyl)-2,2-diphenylacetamide hydrochloride

To a chilled solution of 50.5 g (0.5 mole) of diisopropylamine in 250 ml of water, containing five drops of 2M acetic acid, were slowly added 24.2 g (0,55 mole) of gaseous ethylene oxide maintaining the temperature below 20° C. The mixture was distilled at normal pressure, the water was discarded and the fraction boiling at 188°–190° C. was collected.

Yield 68 g (94%) of 2-(N,N-diisopropylamino)-ethanol. 58 g (0.4 mole) of the above described aminoalcohol was dissolved in 250 ml of methylene chloride and slowly added to a solution of 53.5 g (0.45 mole) of thionyl chloride in 150 ml of methylene chloride. The solution was agitated for 2 hours until no more gases were evolved. After evaporation to drynes the product was crystallised from ethyl acetate.

Yield 72 g (90%) of 2-(N,N-diisopropylamino)-ethylchloride hydrochloride. Melting point 135° C.

60 g (0.3 mole) of the above described halide was dissolved in 100 ml of ethanol and added to 200 ml of a 33% solution of methylamine in ethanol at a temperature below 40° C. The solution was evaporated and the residue was shaken between dilute sodium hydroxide and ether. The ether extract was evaporated whereby the excess of methylamine was removed. The remaining oil was distilled. Boiling point 78°–820° C./8 mmHg.

Yield 41 g (86%) of 2-(N,N-diisopropylaminoethyl)-methylamine.

To a solution of 1.6 g (10 mmole) of the above described N,N-diisopropylaminoethyl-methylamine and 4.0 g (40 mmole) of triethylamine in 10 ml dry ether a solution of 2.5 g (11 mmole) 2,2-diphenylacetylchloride in 10 ml of dry ether was dropwise added. The mixture was stirred at 20° C. for 8 hours. Dilute hydrochloric acid was added and the mixture was shaken vigorously. The water solution was separated, made alkaline with dilute sodium hydroxide and extracted with methylene chloride. The collected organic extracts were shaken with dilute hydrochloric acid and the solution was dried over sodium sulfate. The methylene chloride was evaporated and the residue was crystallised from a mixture of dioxane and ether.

Yield 3.7 g (95%) of N-methyl-N-(2-diisopropylaminoethyl-)-2,2-diphenylacetamide hydrochloride. Melting point 147.5° C.

EXAMPLE 4

N-methyl-N-(3-diisopropylaminopropyl)-2,2 diphenylacetamide.

61 g (0,64 mole) of 3-chloropropanol and 140 g (1.4 moles) of diisopropylamine were heated in an autoclave for 20 hours at 150° C. The reaction mixture was filtered and the filtrate was distilled. Boiling point 97°–99° C./19 mmHg.

Yield 85 g (80%) of 3,(N,N-diisopropylamino)-propanol.

To 85 g (0,53 mole) of the above described aminoalcohol in 200 ml of methylene chloride were added while cooling at 0° C. 119 g (1,0 mole) of thionyl chloride. The mixture was then refluxed for one hour. Methylene chloride and an excess of thionyl chloride was removed in vacuo. The resulting oil was treated with ether and crystallised. The crystals were washed with 25 ml of acetone and dried.

Yield 93 g (85%) of 3-diisopropylaminopropyl chloride hydrochloride. Melting point 112° C.

To a solution of 50 g (1.5 moles) of methylamine in 100 ml ethanol in an autoclave, were slowly added 54 g (0.24 mole) of the above described aminopropyl chloride. The mixture was heated for 5 hours at 100° C. After cooling the mixture was made acidic with dilute hydrochloric acid and the ethanol was evaporated. The residue was made alkaline and extracted with methylene chloride. The solvent was evaporated and the residue was distilled. Boiling point 85° C./12 mmHg.

Yield 30 g (70%) of 3-(N,N-diisopropylamino)-1-methylaminopropan.

To a solution of 3.5 g (20 mmole) of the above described diamine in 20 ml of methylene chloride was slowly added 4.6 g (20 mmole) of 2,2- diphenylacetyl chloride. The mixture was stirred for 12 hours at 20° C. The methylene chloride was distilled and the residue was dissolved in dilute hydrochloric acid and washed with ether. The acidic solution was made alkaline with dilute sodium hydroxide and extracted with ether. The ether was evaporated to dryness at 50° C. to remove all moisture. The product was isolated as an oil.

Yield 3.2 g (44%) of N-methyl-N-(3-diisopropylaminopropyl-)-2,2-diphenylacetamide.

EXAMPLE 5

N-(2-diisopropylaminoethyl)-2,2-diphenyl-2-hydroxyacetamide hydrochloride 10 g (38 mmole) of 2-chloro-2,2-diphenylacetyl chloride were slowly added to a chilled solution of 7.6 ml 5M sodium hydroxide (38 mmole) and 5.3 g (38 mmole) of diisopropylaminoethylamine in 50 ml of methylene chloride. The temperature was kept at 0° C. with good agitation. The mixture was stirred for 1 h. The water solution was discarded and the organic layer was washed with water and dried over anhydrous sodium sulfate. The solution was evaporated to dryness and the remaining oil solidified. The product was dissolved in 2M hydrochloric acid and heated for 10 min on a steambath to hydrolyze the 2-chloro to a hydroxyl group. The solution was chilled to room temperature and was extracted with methylene chloride. The methylene chloride solution was evaporated and the product was crystallised from warm acetone.

Yield 8.3 g (56%) of N-(2-diisopropylaminoethyl)-2,2-diphenyl-2-hydroxy-acetamide hydrochloride. Melting point 178° C.

EXAMPLE 6

N-(3-diisopropylaminopropyl)-2,2-diphenylacetamide hydrochloride 200 g (1 mole) of diisopropylaminoethyl chloride, hydrochloride, were dissolved in 1 liter of water and neutralized by the addition of sodium hydroxide 5M to pH 8.49 g (1 mole) of sodium cyanide were added and the solution was agitated for 24 hours. The product separated as an oil which was collected, dried and distilled. Boiling point 102° C./12 mmHg.

Yield 143 g (93%) of 3-(N,N-diisopropylamino)propionitrile.

98 g (0.62 moles) of the above described nitrile were dissolved in 750 ml of ethanol containing 50 ml of concentrated aqueous ammonia and 7 g of Rhodium on aluminium oxide catalyst. The mixture was hydrogenated at 6 bar pressure for 20 hours. The catalyst was separated by filtration and the solution was evaporated at 40° C. The remaining oil was distilled. Boiling point 70° C./8 mmHg.

Yield 60 g (60%) of 3-(N,N-diisopropylamino)-propylamine.

6.9 g (30 mmoles) of 2,2-diphenylacetyl chloride in 50 ml methylene chloride was slowly added at 0° C. to a solution of 9.2 g (60 mmoles) of the above described diamine in 50 ml of methylene chloride. The solution was agitated for 8 hours at 20° C. and evaporated to dryness. The residue was dissolved in 25 ml of 2M hydrochloric acid. The solution was washed with ether and then extracted three times with methylene chloride and evaporated. The product was crystallised from butanone.

Yield 5.7 g (50%) of N-(3-diisopropylaminopropyl)-2,2-diphenylacetamide hydrochloride. Melting point 182° C.

EXAMPLE 17

N-methyl-N-[3-(N-methyl-N-tert-butyl-amino)-propyl]-2,2-diphenylacetamide hydrochloride To a solution of 4.0 g (25 mmole) of 1-(N-methyl-N-tertbutylamino)-3-methylaminopropane (prepared according to Example 5) in 50 ml of dry acetone containing 4.8 g (35 mmole) of potassium carbonate dried at 110° C., were added 5.8 g (25 mmole) of 2,2-diphenylacetyl chloride at 0° C. The mixture was stirred for 0.5 hour and then refluxed for 3 hours. The inorganic salts were filtered and the solution was evaporated. The remaining oil was dissolved in 5M hydrochloric acid and washed with ether. The acidic water solution was extracted with methylene chloride and evaporated. The remaining oil was crystallised from acetone/ether.

Yield 8.3 g (85%) of N-methyl-N-[3-(N-methyl-N-tert-butylamino-)-propyl-]-2,2-diphenylacetamide hydrochloride. Melting point 170° C.

EXAMPLE 8

N-(2-diisopropylaminoethyl)-2-phenyl-2-(2-hydroxyphenyl)acetamide hydrochloride 40 g of mandelic acid (263 mmole) and 28 g of phenol (300 mmole) in 60 ml of 70% sulfuric acid were heated for 20 min on a steam bath. The solution was poured into cold water and extracted with ether. The ether solution was washed with dilute sodium hydroxide, dried and evaporated to dryness. The product was recrystallised twice from ethanol.

Yield 23.2 g (42%) of 3-phenyl-2[3H]-benzfuranone.

To a solution of 3.2 g (15 mmole) 2-(N,N-diisopropylamino)ethylamine in 25 ml of hydrochloric acid were added 4.2 g (20 mmole) of the above described lactone in 25 ml of chloroform. The mixture was stirred for 20 hours at room temperature. The solution was evaporated and the residue was crystallised from butanone.

Yield 5.7 g (94%) of N-(2-diisppropylaminoethyl-)-2-phenyl-2-(2-hydroxyphenyl)-acetamide hydrochloride. Melting point 181° C.

EXAMPLE 9

N-2-(1-piperidinyl)-ethyl-3,3-diphenyl-propionamide

To a solution of 2.56 g (20 mmole) N-(2-aminoethyl)-piperidine in 30 ml dioxane were, at room temperature, added a solution of 4.95 g of 3,3-diphenylpropionyl chloride (20 mmole) in 20 ml of dioxane. The mixture was stirred at 20 for 8 hours and the dioxane was distilled. The residue was dissolved in 50 ml of methylene chloride. The discoloured solution was treated with 10 g of aluminia, shaken and filtered. The filtrate was evaporated and the residue was crystallised from a mixture of ethyl acetate/hexane.

Yield 4.8 g (71%) of N-2-(1-piperidino-)-ethyl-3,3-diphenylpropionamide. Melting point 94° C.

EXAMPLE 10

Alternatively the compound N-(2-diisopropylaminoetyl)-2,2-diphenylacetamide can be prepared according to the following methods a) or b).

a) 21 g (0.1 mole) of diphenylacetamide and 4 g (0.1 mole) of sodium amide were refluxed in 250 ml of toluene for 6 hours under nitrogen, 16.3 g (0.1 mole) of N,N-diisopropylaminoethylchloride was slowly added to the mixture and the whole was further heated over night.

The chilled reaction mixture was extracted with dilute hydrochloric acid. The aqueous solution was made alkaline with dilute sodium hydroxide and extracted with methylene chloride. The product was purified on HPLC using silica gel and hexan:ether 1:5 as eluent. After precipitation of the compound with hydrogen chloride in ether, the hydrochloride was crystillised from butanone.

Yield 14.9 g of (30%) N-(2-diisopropylaminoetyl)-2,2-diphenylacetamide. Melting point 182° C.

b) 31.8 g (0.15 mole) of diphenylacetic acid and 19.6 g (0.12 mole) of N-(2-diisopropyl)aminoethylamine was heated at 150° C. for 16 hours and water was distilled off continuously. The reaction mixture was allowed to cool, dissolved in a mixture of 100 ml of methylene chloride and 200 ml of 1M sodium hydroxide under vigorous stirring. The methylene chloride layer was washed with 2×50 ml of water and shaken with hydrochloric acid. The ion pair solution was dried over sodium sulphate. The methylene chloride was evaporated and the residue was crystallised from butanone.

Yield 30.5 g (68%) of N-(2-diisopropylaminoethyl)-2,2-diphenylacetamide. Melting point 182° C.

EXAMPLE 11

N-(2-hydroxyethyl)-N-methyl-2,2-diphenylacetamide

To a mixture of 9 g (0.12 mole) of N-methylaminoethanol and 17 g (0.12 mole) of potassium carbonate in 100 ml of acetone was added 25 g (0.11 mole) 2,2-diphenylacetylchloride. The mixture was stirred for 0.5 hours and then refluxed for 3 hours. The mixture was cooled and filtered. The salt was extracted with 3×125 ml methylene chloride. The collected organic extracts were evaporated.

Yield 26 g (88%) of N-(2-hydroxyethyl)-N-methyl-2,2-dipenylacetamide. Melting point 144° C.

N-(2-chloroethyl)-N-methyl-2,2-diphenylacetamide

To a solution of 26 g (0.1 mole) of N-(2-hydroxyethyl)-N-methyl-2,2-diphenylacetamide in 25 ml of methylene chloride was slowly added 24 g (0.2 mole) of thionyl chloride at 0° C. The solution was stirred for 0.5 h and warmed at 50° C. for 2 hours. The solution was evaporated, the residue was dissolved in 25 ml of toluene and the solution was evaporated. The residue was washed with hexane and used without further purification.

15 g (0.05 mole) of N-(2-chloroethyl)-N-methyl-2,2-diphenylacetamide together with 50 ml of ethanol and 15 g (0.15 mole) of diisopropylamine is heated in a pressure vessel at 120° C. for 48 hours. After cooling the excess of amine was evaporated. The residue was shaken with a mixture of ether and dilute hydrochloric acid. The water solution was separated, made alkaline with dilute sodium hydroxide and extracted with methylene chloride. The methylene chloride solution was shaken with dilute hydrochloric acid and the ion pair solution was dried over sodium sulfate. The methylene chloride was evaporated and the residue was crystallised from a mixture of dioxane and ether.

Yield 9.4 g (48%) of N-methyl-N-(2-diisopropylaminoethyl-)-2,2-diphenylacetamide hydrochloride. Melting point 147.5° C.

EXAMPLE 12

In essentially the same way the following compounds were prepared:

| Ar | R1 | R2 | n | m | R4 | R5 | MP °C. |
|---|---|---|---|---|---|---|---|
| Ph | H | Me | 0 | 3 | Et | Et | 144 |
| Ph | OH | Me | 0 | 3 | iPr | iPr | oil base |
| Ph | H | Me | 0 | 3 | Me | Me | 156 |
| Ph | H | Me | 0 | 3 | 2-Bu | 2-Bu | oil base |
| Ph | H | Me | 1 | 3 | Et | Et | oil |
| Ph | OH | Me | 0 | 3 | iPr | iPr | oil base |
| Ph | Me | Me | 0 | 3 | Et | Et | 182 |
| Ph | Me | H | 0 | 3 | iPr | iPr | 175 |
| Ph | H | H | 1 | 3 | iPr | iPr | 182 |
| Ph | H | H | 0 | 3 | Me | Me | 188 |
| Ph | Me | Me | 0 | 2 | iPr | iPr | 204 |
| Ph, Bz | H | Me | 0 | 2 | iPr | iPr | 114 |
| Ph, 2-OH | H | Me | 0 | 2 | iPr | iPr | 196 |
| Ph | H | Et | 0 | 2 | iPr | iPr | 166 |
| Ph | H | H | 0 | 2 | iPr | iPr | 182 |
| Ph | H | H | 0 | 2 | Et | Et | 144 |
| Ph | H | H | 0 | 2 | Me | Me | 184 |
| Ph | H | H | 0 | 2 | Me | iPr | 130 |
| Ph | H | H | 0 | 2 | Me | tBu | 141 |
| Ph | H | H | 0 | 2 | Et | iBu | 56 base |
| Ph | H | H | 1 | 2 | iPr | iPr | 149 |
| Ph | H | Me | 0 | 3 | 1-(2,6-diMe-)piperidyl | | 180 |
| Ph | H | Me | 0 | 2 | 1-(2,2,6,6-tetraMe)piperidyl | | 218 |

EXAMPLE A

Preparation of Tablets

| | Ingredients | mg/tablet |
|---|---|---|
| 1. | Compound according to the invention | 2.0 |
| 2. | Cellulose microcrystalline | 57,0 |
| 3. | Calcium hydrogen phosphate | 15,0 |
| 4. | Sodium starch glycolate | 5,0 |
| 5. | Silicon dioxide, colloidal | 0,25 |
| 6. | Magnesium stearate | 0,75 |

-continued

| Ingredients | mg/tablet |
|---|---|
| | 80.0 mg |

The compound 1 according to the invention is mixed with ingredients 2, 3, 4 and 5 for about 10 minutes. The magnesium stearate is then added, the resultant mixture being mixed for about 5 minutes and then compressed into tablet form with or without filmcoating.

EXAMPLE B

Preparation of Capsules

| | Ingredients | mg/capsule |
|---|---|---|
| 1. | Compound according to the invention | 2 |
| 2. | Lactose | 186 |
| 3. | Corn starch | 20 |
| 4. | Talc | 15 |
| 5. | Magnesium stearate | 2 |
| | | 225 mg |

The compound 1 according to the invention is mixed with ingredients 2 and 3 and then milled. The resulting mixture is then mixed with ingredients 4 and 5 and then filled into capsules of appropriate size.

As stated above the compounds according to this invention have an inhibiting action on the contractile state of the urinary bladder, revealed by their ability to inhibit contractile effects on the urinary bladder.

These properties indicate that the compounds according to this invention are of potential use in the treatment of disorders of the urinary bladder, such as hyperreflexia, urgency, urge incontinence, unstable detrusor, hyperactive detrusor, enuresis, cystitis and detrusor-sphincter dyssynergia. The following experiments illustrate the pharmacological effect of the compounds.

A large number of compounds according to this invention has been tested on the inhibiting effect on electrically stimulated urinary bladder strips. The effects of some of the more interesting compounds are presented in Table 1. This table also includes effects of the commersially available drugs atropine, terodiline and oxybutynin. The effects on the bladder have been compared with possible effects on other organs (Table 1). The results clearly show that the compounds included in the invention are more selective for the urinary bladder than for some other organ systems, especially the salivary glands.

The anticholinergic effect and the inhibitory effect on electrically induced contractions (of which about 50% is cholinergically mediated) in the urinary bladder were studied on isolated bladder strips from the rabbit and man.

Carbachol was used as an agonist and was added to the organ bath cumulatively. The electrically induced contractions were submaximal and reproducible for a long time period. The methods are described in detail by K.-E. Andersson in Scand. J. Urol. Nephrol., 1984, Suppl. 87, 13-20.

The effects of the compounds on the isolated, rabbit portal vein, which has been used as a reference blood vessel, were studied on electrically induced, submaximal contractions. The method is described in detail by M.E. Holman et al. in J. Physiol., 1968, 166, 111-132.

The effects on heart were investigated by using isolated, rabbit papillary muscles, which were electrically stimulated at a submaximum frequency. The contraction amplitude was recorded. The method is described in detail and modified for rabbit by J. G. Dobson et al. in Amer. J. Physiol., 1974, 227, 1452-1457.

For studying the mydriatic effect of the compounds unanaesthetized albino mice were used. The substance was given intravenously in different doses and the pupil diameter was measured by means of a microscope every tenth minute until the effect disappeared. The method is described in detail by de Jongh et al. in Arch. Intern. Pharmacodyn., 1955, 103, 100-106.

The human salivary glands were obtained from patients undergoing operation for treatment of cancer in these glands. As the radioligand by which the muscarinic receptors were labelled, QNB was used. The method is described in detail by S. Batra et al. in Psychopharmacology, 1986, 90, 1-4.

TABLE 1

| Substance | [1]El. stim. rabbit urinary bladder IC50 ($\mu$M) | Carbachol stim. rabbit urinary bladder $K_D$ ($\mu$M) | El. stim. papillary muscle, % inhibition of 1 $\mu$M | Mydriatic effect, % dilatation by 1 mg/kg i.v. | El. stim. portal vein % inhibition by 1 $\mu$M | Selectivity factor for human urinary bladder in comparison with human salivary gland[2] |
|---|---|---|---|---|---|---|
| Atropine | 0.003 | 0.002 | 5 | 524 | 20 | 30 |
| Terodiline | 14.5 | 0.22 | 14 | 1 | 4 | 93 |
| Oxybutynin | 2.9 | 0.006 | 3 | 95 | 6 | 340 |
| Example No 10 | 5.3 | 0.11 | 0 | 11 | 10 | 6 |
| Example No 3 | 8.5 | 0.06 | 8 | 2 | 10 | 6 |
| Example No 4 | 35.2 | 0.55 | 9 | 0 | 4 | 5 |
| Example No 7 | 25.7 | 2.90 | 0 | 0 | 4 | 2 |

[1]Only about half of the contractile response is mediated by cholinergic nerves.
[2]The selectivity factor is a quotient of the inhibitory concentration of the substance on the isolated human urinary bladder and the human salivary gland. The lower the figure is in this column the higher selectivity for the human urinary bladder.

We claim:
1. Compounds having the general formula II:

$$\begin{array}{c} Ar \\ \diagdown \\ \phantom{Ar}C-CON-CH_2-CH_2-N \\ \diagup \\ Ar \end{array} \begin{array}{c} R^1 \quad R^2 \\ | \quad\quad | \\ \\ \end{array} \begin{array}{c} R^7 \\ \diagup \\ \\ \diagdown \\ R^8 \end{array}$$

wherein
Ar is a phenyl group which is optionally substituted with hydroxy;
$R^1$ is hydrogen or lower alkyl;
$R^2$ is hydrogen or lower alkyl;
$R^7$ and $R^8$ which can be the same or different, are lower alkyl, wherein one or both of $R^7$ and $R^8$ is branched and the total number of carbon atoms in $R^7$ and $R^8$ is at least 6;

their salts with physiologically acceptable acids and, when the compounds can be in the form of optical isomers, the racemic mixture and the individual enantiomers.

2. Compounds according to claim 1 characterized in that $R^7$ and $R^8$ are isopropyl.

3. The compounds of claim 1, selected from the group consisting of:

N-methyl-N-(2-diisopropylaminoethyl)-2,2-diphenylacetamide

N-(2-diisopropylaminoethyl)-2,2-diphenylacetamide

N-methyl-N-(2-diisopropylaminoethyl)-2-methyl-2,2-diphenylacetamide.

4. A pharmaceutical composition comprising a compound according to claim 1 with a pharmaceutically acceptable carrier.

5. A pharmaceutical composition comprising a compound according to claim 2 with a pharmaceutically acceptable carrier.

6. A pharmaceutical composition comprising a compound according to claim 3 with a pharmaceutically acceptable carrier.

* * * * *